United States Patent [19]

Fischer et al.

[11] 4,385,182
[45] May 24, 1983

[54] THIOXANTHONECARBOXYLIC ACIDS AND THIOXANTHONECARBOXYLIC ACID DERIVATIVES

[75] Inventors: Walter Fischer; Vratislav Kvita, both of Reinach; Hans Zweifel; Louis Felder, both of Basel, all of Switzerland

[73] Assignee: Ciba-Geigy Corporation, Ardsley, N.Y.

[21] Appl. No.: 258,267

[22] Filed: Apr. 28, 1981

[30] Foreign Application Priority Data

May 6, 1980 [CH] Switzerland ............... 3519/80

[51] Int. Cl.³ .................................... C07D 335/16
[52] U.S. Cl. .................................... 549/27; 260/349; 544/79; 544/130; 544/132; 544/141; 544/145; 546/187; 546/202
[58] Field of Search ............... 549/27; 260/349; 544/79, 130, 132, 141, 145; 546/187, 202; 548/525

[56] References Cited

U.S. PATENT DOCUMENTS 3,642,997  2/1972  Shen et al. ............... 549/27 X
3,904,647  9/1975  Pfister et al. ............... 260/328
4,348,530  9/1982  Kvita et al. ............... 549/27

FOREIGN PATENT DOCUMENTS 2811755  7/1978  Fed. Rep. of Germany.
46-31731  4/1971  Japan.
49-32796  3/1974  Japan.
1458185   6/1976  United Kingdom.

*Primary Examiner*—Richard Raymond
*Attorney, Agent, or Firm*—Harry Falber

[57] ABSTRACT

Novel thioxanthonecarboxylic acids and thioxanthonecarboxylic acid derivatives of the formula I

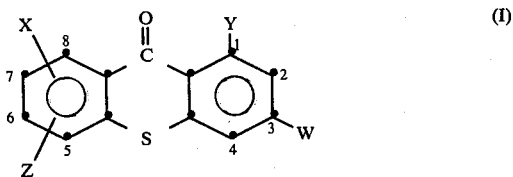

in which Y is —COOH, —CO-halogen, —CN or a carboxylic acid ester, thioester or amide group and X, Z and W are as defined in the patent claim, are described. The compounds of the formula I in which Y is other than —CO—halogen are suitable as sensitizers for photo-crosslinkable polymers or as initiators for photopolymerization of ethylenically unsaturated compounds or for photo-chemical crosslinking of polyolefins. The acid halides of the formula I are starting materials for the preparation of the corresponding nitriles and carboxylic acid esters, thioesters and amides.

6 Claims, No Drawings

THIOXANTHONECARBOXYLIC ACIDS AND THIOXANTHONECARBOXYLIC ACID DERIVATIVES

The present invention relates to novel thioxanthonecarboxylic acids and thioxanthonecarboxylic acid derivatives, in particular thioxanthonecarboxylic acid esters, thioesters, amides and nitriles, a process for their preparation and their use as sensitisers for photo-crosslinkable polymers, or as initiators, preferably as mixtures with amines, for photo-polymerisation of ethylenically unsaturated compounds or for photo-chemical crosslinking of polyolefins.

It is known that halogen-free or halogenated, especially chlorinated, thioxanthones are suitable as sensitisers for photo-chemical crosslinking reactions. A prerequisite for the sensitiser to be used successfully in this manner is that it has a good compatibility in the polymer, i.e. the sensitiser must be miscible with the polymer up to high concentrations. The sensitisers must also be readily soluble in the solvents used during processing of the polymers. The abovementioned thioxanthones do not fulfil these requirements in all respects; in particular, they demix readily in the polymer, which means that their sensitiser action is greatly impaired, or their sensitiser action in inadequate.

It is also known that photo-polymerisation of ethylenically unsaturated compounds can be initiated by aromatic ketones of the benzophenone, anthraquinone, xanthone and thioxanthone type. It is furthermore known, from U.S. Pat. No. 3,759,807, that the initiator action of such aromatic ketones can be accelerated by adding organic amines. Since these amines in most cases do not have an initiator action by themselves, they act as activators or accelerators when combined with aromatic ketones. This is of great importance from an industrial point of view, since the rate of production of photo-chemically cured coatings or printing inks depends, in particular, on the rate of polymerisation of the unsaturated compound.

Novel thioxanthone derivatives of the formula I

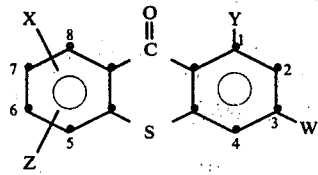

in which W is halogen, -CN, -OH, -N(R$_1$)(R$_2$), -NO$_2$, phenylsulfonyl, toluylsulfonyl, C$_{1-4}$-alkylsulfonyl, C$_{1-10}$-alkoxy, C$_{1-10}$-alkylthio, C$_{1-12}$-halogenoalkylthio, phenoxy, toluyloxy, phenylthio, chlorophenylthio, toluylthio, azido, 4,5-bis-C$_{1-2}$-alkoxycarbonyl-1,2,3-triazolyl, C$_{3-5}$-alkenyloxy, C$_{3-5}$-alkynyloxy, 1-nitroalkyl having 1-5 C atoms, -CH(COOR$_3$)$_2$, -C(COOR$_3$)$_2$(CH$_3$), -CH(CN)(COOR$_3$), -C(CN)(COOR$_3$)(CH$_3$), -CH(CN)$_2$, -C(CN)$_2$(CH$_3$), -CH$_2$COOH or -CH(CH$_3$)(COOH), Y is -CO-halogen, -COOR$_1$, -COSR$_1$, -CON(R$_1$)(R$_2$), -CO-piperidyl, -CO-pyrrolidinyl, —CO— morpholinyl or -CN, Z is hydrogen, halogen, -OH or alkyl, alkoxy, alkylthio or N,N-dialkylamino having in each case 1-4 C atoms in the alkyl groups, X can have the same meaning as W or is hydrogen, -SO$_3$H, alkyl, -NHCO-alkyl or -CO-alkyl having in each case 1-4 C atoms in the alkyl group, -COOR$_1$, -COSR$_1$, -CON(R$_1$)(R$_2$), -CO-piperidyl, —CO— pyrrolidinyl or -CO-morpholinyl, R$_1$ is hydrogen, C$_{1-20}$-alkyl, C$_{5-12}$-cycloalkyl, phenyl, naphthyl or benzyl, R$_2$ is hydrogen or C$_{1-20}$-alkyl and R$_3$ is methyl or ethyl, have now been found.

The compounds of the formula I in which Y is not -CO-halogen are outstandingly suitable for use as sensitisers for photo-crosslinkable polymers. In particular, they have a good compatibility with the polymer, a good solubility in the customary organic solvents and an increased photosensitivity. Furthermore, the UV absorption can be influenced so that said compounds according to the invention (Y is not -CO-halogen) also have a sensitising action when irradiated with longwave UV light (up to about 450 nm), and thus effect crosslinking of the photosensitive polymers. The compounds mentioned are also suitable, preferably when mixed with organic amines, as initiators for photo-polymerisation of ethylenically unsaturated compounds or for photochemical crosslinking of polyolefins.

The compounds of the formula I in which Y is —CO— halogen are starting substances for the preparation of the corresponding thioxanthonecarboxylic acid esters, thioesters, amides and nitriles.

A halogen atom X, Y or W can be, for example, fluorine or bromine, and in particular chlorine. A halogen substituent in a halogenoalkylthio group X or Y is, for example, bromine, but in particular chlorine and especially fluorine.

An alkyl, alkoxy, alkylthio, alkenyloxy or alkynyloxy group X, Z, W, R$_1$ or R$_2$ and an alkyl radical in a group X, Z or W can be straight-chain or branched. Examples of alkyl, alkoxy, alkylthio, alkylsulfonyl, -N(R$_1$)(R$_2$), -NH-CO-alkyl, -CO-alkyl, halogenoalkylthio, alkenyloxy, alkynyloxy and 1-nitroalkyl groups X, Z, W, R$_1$ or R$_2$ of the type defined are: methyl, ethyl, n-propyl, isopropyl, n-butyl, sec.-butyl, tert.-butyl, n-pentyl, 2- or 3-pentyl, n-hexyl, n-heptyl, 2- or 3-heptyl, n-octyl, n-nonyl, n-decyl, 2-decyl, n-dodecyl, n-tetradecyl, n-hexadecyl, n-octadecyl, tridec-7-yl, heptadecyl-9-yl, 2,6,10-trimethyldodecyl and 2,6,10,14-tetramethylhexadecyl; methoxy, ethoxy, n-propoxy, isopropoxy, n-butoxy, n-pentyloxy, n-hexyloxy, n-octyloxy and n-decyloxy; methylthio, ethylthio, n-propylthio, n-butylthio, 2-butylthio, tert.-butylthio, n-hexylthio, n-heptylthio, n-nonylthio, n-decylthio and n-dodecylthio; methylsulfonyl, ethylsulfonyl and n-propylsulfonyl; -NH$_2$, methylamino, ethylamino, n-propylamino, n-butylamino, n-hexylamino, n-octylamino, n-decylamino, N,N-dimethylamino, N,N-diethylamino, N-methyl-N-ethylamino, N,N-di-n-propylamino, N,N-di-n-butylamino, N,N-di-n-hexylamino and N,N-di-n-octylamino; acetylamino, propionylamino and butyrylamino; acetyl, propionyl and butyryl; -SCF$_3$, -SCH$_2$CH$_2$Cl, -SCH$_2$CH$_2$Br, -SCH$_2$CF$_3$, -SCH$_2$CH$_2$(CF$_2$)$_3$CF$_3$, -SCH$_2$CH$_2$(CF$_2$)$_5$CF$_3$ and -SCH$_2$CH$_2$(CF$_2$)$_7$CF$_3$; allyloxy, methallyloxy, 2-butenyloxy and 4-pentenyloxy; 2-propynyloxy, 3-butynyloxy and 4-pentynyloxy; and nitromethyl, 1-nitroethyl, 1-nitro-n-propyl, 2-nitro-2-propyl, 1-nitro-n-butyl and 1-nitro-n-pentyl.

R$_1$ and R$_2$ in a -COOR$_1$, -COSR$_1$ or -CON(R$_1$)(R$_2$) group X preferably have the same meaning as in the radicals Y.

An alkyl group R$_1$ preferably has 1-12 and in particular 1-4 C atoms. A C$_{5-12}$-cycloalkyl radical R$_1$ is, for example, cyclopentyl, cyclooctyl or cyclododecyl, or, in particular, cyclohexyl. An alkoxy or alkylthio group X or W preferably has 1–6, and in particular 1–4, C atoms. $R_2$ is preferably $C_{1-4}$-alkyl or hydrogen. A toluylsulfonyl, toluyloxy, chlorophenylthio or toluylthio group X or W is preferably the p-toluylsulfonyl, p-toluyloxy, p-chlorophenylthio or p-toluylthio group. A halogenoalkylthio group W or X is preferably a $-SCH_2CH_2(CF_2)_{\overline{n}}F$ group, in which n is 4, 6, 8 or 10. A $C_{3-5}$-alkenyloxy or $C_{3-5}$-alkynyloxy radical W or X is, in particular, allyloxy, methallyloxy or 2-propynyloxy. A 1-nitroalkyl group W or X preferably has 1–3 C atoms. An alkyl group X or Z, an alkylsulfonyl group W or X, a -NHCO-alkyl or -CO-alkyl group X and an alkoxy, alkylthio or N,N-dialkylamino group Z advantageously has in each case 1 or 2 C atoms in the alkyl radical.

Compounds of the formula I in which W is halogen, —CN, —$N(R_1)(R_2)$, in which $R_1$ and $R_2$ independently of one another are hydrogen or $C_{1-4}$-alkyl, or $NO_2$, phenylsulfonyl, p-toluylsulfonyl, $C_{1-4}$-alkylsulfonyl, $C_{1-4}$-alkoxy, $C_{1-4}$-alkylthio, $-SCH_2CH_2(CF_2)_{\overline{n}}F$, in which n is 4, 6, 8 or 10, phenoxy, p-toluyloxy, phenylthio, p-chlorophenylthio, p-toluylthio, azido, 4,5-bis-$(C_{1-2}$-alkoxycarbonyl)-1,2,3-triazolyl, 1-nitroalkyl having 1–5 C atoms, $-CH(COOR_3)_2$, $-C(COOR_3)_2(CH_3)$, $-CH(CN)(COOR_3)$, $-C(CN)(COOR_3)(CH_3)$, $-CH(CN)_2$, $-C(CN)_2(CH_3)$, $-CH_2COOH$ or $-CH(CH_3)(COOH)$, Y is -COOH, -CN, -COOalkyl having 1–8 C atoms in the alkyl moiety, -COSalkyl having 1–4 C atoms in the alkyl moiety or $-CON(R_1)(R_2)$, in which $R_1$ and $R_2$ independently of one another are hydrogen or $C_{1-4}$-alkyl, Z is hydrogen, halogen or $C_{1-4}$-alkyl, X is hydrogen, $C_{1-4}$-alkyl, $C_{1-4}$-alkoxy, -COOalkyl having 1–8 C atoms in the alkyl moiety, -COSalkyl having 1–4 C atoms in the alkyl moiety or $-CON(R_1)(R_2)$, in which $R_1$ and $R_2$ independently of one another are hydrogen or $C_{1-4}$-alkyl, and $R_3$ is methyl or ethyl, are preferred.

Further preferred compounds of the formula I are those in which X is hydrogen, halogen, in particular bromine or chlorine, alkyl, alkoxy or alkylthio having in each case 1–4, and preferably 1 or 2, C atoms, or acetylamino, Z is hydrogen, halogen, in particular bromine or chlorine, or alkyl having 1–4, and in particular 1 or 2, C atoms, W is chlorine, bromine, $-NH_2$, $-NO_2$, $C_{1-4}$-alkylsulfonyl, in particular $C_{1-2}$-alkylsulfonyl, phenylsulfonyl, p-toluylsulfonyl, $C_{1-4}$-alkoxy, $C_{1-4}$-alkylthio, p-chlorophenylthio or 2-nitro-2-propyl and Y is -COOH, —CN, —COO-alkyl having 1–8 C atoms in the alkyl moiety or $-CON(R_1)(R_2)$, in which $R_1$ and $R_2$ independently of one another are $C_{1-4}$-alkyl or hydrogen. X is preferably bonded in the 7-position, whilst Z is preferably bonded in the 6-position.

Compounds of the formula I in which X is hydrogen, or methyl which is bonded in the 7-position, Z is hydrogen, W is chlorine, $-NO_2$ or phenylsulfonyl and Y is -COOH or -COOalkyl having 1–8 C atoms, are particularly preferred. Compounds of the formula I in which X and Z are each hydrogen, W is the nitro group and Y is -COOH, $-COOCH_3$ or $-COOC_2H_5$, are especially preferred.

The compounds of the formula I can be prepared, for example, by a process which comprises cyclising a compound of the formula II

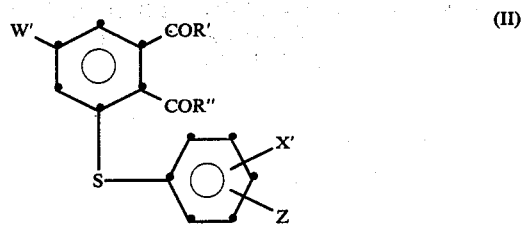

in which R' and R" are each -OH or together are -O-, W' is halogen, -CN, -OH, $-N(R_1)(R_2)$, in which $R_1$ and $R_2$ are other than hydrogen, or $-NO_2$, phenylsulfonyl, toluylsulfonyl, $C_{1-4}$-alkylsulfonyl, $C_{1-10}$-alkoxy, $C_{1-10}$-alkylthio, $C_{1-12}$-halogenoalkylthio, phenoxy, toluyloxy, phenylthio, p-chlorophenylthio, toluylthio, azido, $C_{3-5}$-alkenyloxy, $C_{3-5}$-alkynyloxy, 1-nitroalkyl having 1–5 C atoms, $-CH_2COOH$ or $-CH(CH_3)(COOH)$, X' is hydrogen, halogen, -CN, -OH, $-NO_2$, $-SO_3H$, -COOH, phenylsulfonyl, toluylsulfonyl, $C_{1-4}$-alkylsulfonyl, $C_{1-4}$-alkyl, $C_{1-10}$-alkoxy, $C_{1-10}$-alkylthio, $-N(R_1)(R_2)$, in which $R_1$ and $R_2$ are other than hydrogen, or $C_{1-12}$-halogenoalkylthio, phenoxy, toluyloxy, phenylthio, p-chlorophenylthio, toluylthio, azido, $C_{3-5}$-alkenyloxy, $C_{3-5}$-alkynyloxy, 1-nitroalkyl having 1–5 C atoms, $-CH_2COOH$, $-CH(CH_3)(COOH)$, -CO-alkyl having 1–4 C atoms in the alkyl moiety, $-COOR_1$, $-COSR_1$ or $-CON(R_1)(R_2)$, in which $R_1$ and $R_2$ are other than hydrogen, and Z is as defined under formula I, to give a compound of the formula Ia

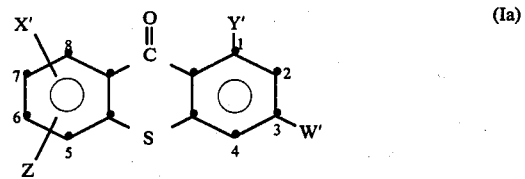

in which Y' is -COOH and X', Z and W' are as defined above, and, if desired, the compound of the formula Ia is then converted into a compound of the formula I in which Y, W and/or X have a different meaning to Y', W' and/or X'.

Compounds of the formula I can also be prepared in a manner known per se by a modified process, which comprises reacting a compound of the formula III

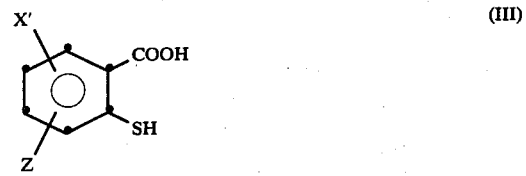

with a compound of the formula IV

in the presence of an organic or inorganic base, such as triethylamine, pyridine, sodium hydroxide, acetate, fluoride, bicarbonate or carbonate or potassium hydroxide, acetate, fluoride, bicarbonate or carbonate, or reacting alkali metal salts of compounds of the formulae III and IV, to give a compound of the formula V

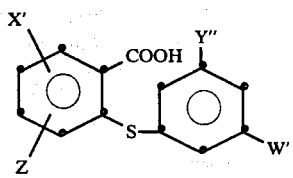
(V)

and cyclising the compound of the formula V, if necessary after first converting it into the acid chloride, to give a compound of the formula I in which Y" is other than -CO-halogen. If desired, the compounds thus obtained can then be converted into compounds of the formula I in which Y, W and/or X have a different meaning to Y", W' and/or X', as described below. In the formulae III, IV and V, X', Z and W' are as defined above, Q is a halogen atom, such as fluorine, chlorine or bromine, or -NO₂, and Y" is -CN, -COOR₁, -COSR₁, -CON(R₁)(R₂), -CO-piperidyl, -CO-pyrrolidinyl or -CO-morpholinyl.

The cyclisation of the compounds of the formulae II and V is advantageously carried out in the presence of a proton acid or a Lewis acid. Examples of suitable proton acids are polyphosphoric acid, where relevant as a mixture with phosphorus oxychloride, and chlorosulfonic and sulfuric acid. Suitable Lewis acids are, for example, aluminium trichloride and boron trifluoride. The cyclisation is preferably carried out in the presence of polyphosphoric acid or aluminium trichloride, and preferably at temperatures between about 0° and 240° C., in particular between about 100° and 200° C.

If the cyclisation is carried out in the presence of a Lewis acid, such as aluminium trichloride, an inert organic solvent is advantageously present. Solvents are, in particular, chlorinated aliphatic or aromatic hydrocarbons, such as methylene chloride, 1,2-dichloroethane, 1,2,3-trichloropropane, 1,1,2,2-tetrachloroethane and o-dichlorobenzene; and n-pentane, n-hexane, nitromethane, nitrobenzene and carbon disulfide. If a proton acid is the cyclising agent, the cyclisation is advantageously carried out in an excess of acid, in particular excess polyphosphoric acid.

Finally, compounds of the formula I can also be obtained in a manner known per se, by a process which comprises reacting a compound of the formula VI

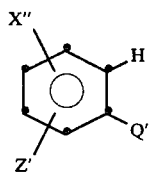
(VI)

with a compound of the formula VII

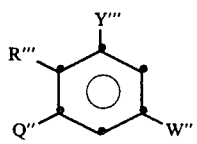
(VII)

or a corresponding acid chloride, in the presence of a Lewis acid or proton acid, preferably of the type defined above, to give a compound of the formula VIII

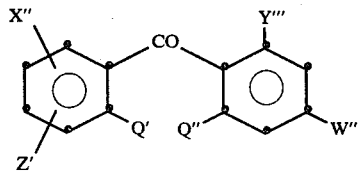
(VIII)

and cyclising the compound of the formula VIII in the presence of an inorganic sulfide, in particular an alkali metal sulfide or hydrosulfide or alkaline earth metal sulfide or hydrosulfide, preferably sodium sulfide. If desired, the compounds thus obtained can then be converted into compounds of the formula I in which X, Z, Y and/or W have a different meaning to X", Z', Y"" and/or W" in a manner known per se.

In the above formulae VI to VIII, R'" is -COOH or, together with Y"", an anhydride group, X" is a group X, with the exception of -OH, NH₂, -NHR₁, -CONH₂, -CONHR₁ or -CO-alkyl, Z' is a group Z, with the exception of -OH, Y"" is a group Y, with the exception of -CO-halogen, -CONH₂ and -CONHR₁, or, together with R'", is an anhydride group, W" is a group W, with the exception of -OH, -NH₂ or -NHR₁ and Q' and Q" independently of one another are halogen atoms, such as chlorine or bromine, or nitro groups. Q' and Q" are preferably each chlorine or nitro.

Conversion of the groups X', X", Z', Y', Y", Y"'W' and/or W" into different groups X, Z, Y and/or W can in some cases take place simultaneously, but is generally carried out by a stepwise procedure. These conversion reactions are known per se and can be summarised as follows:

1. Y=—CO-halogen and/or W=halogen

By treatment of compounds of the formula I in which Y is —COOH and/or W is —NO₂ with suitable halogenating agents, such as oxalyl chloride, thionyl chloride, phosphorus oxychloride, phosphorus oxybromide or phosphorus pentachloride. Carboxyl groups X' are simultaneously halogenated.

2. Y and in some cases X=—COOR₁, —COSR₁, —CON(R₁)(R₂), —CO-piperidyl, —CO-pyrrolidinyl or —CO-morpholinyl By reaction of compounds of the formula I or of the acid halides obtained according to (1) with a compound HY₁, or by reaction of alkali metal salts or alkaline earth metal salts of a compound of the formula I with a halide Hal-Y₁ in the presence of a base, such as a tertiary amine, for example triethylamine or pyridine. Y₁ is —OR₁, —SR₁, —N(R₁)(R₂), piperidyl, pyrrolidinyl or morpholinyl.

3. Y and in some cases X and/or W are —CN

By reaction of the acid halides or halides obtained according to (1) with aqueous or alcoholic ammonia solution and dehydration of the resulting amides with a suitable agent which detaches water, such as POCl₃ or SOCl₂.

4. X and/or W=N(R₁)(R₂) or —NHCO-alkyl

By reduction of nitro groups X and/or W and, where relevant, subsequent alkylation or reaction with corresponding alkanoyl halides in the presence of a base, such as a tertiary amine, for example triethylamine or pyridine.

5. X and/or W=—OH

By reaction of compounds of the formula I in which X and/or W=—NO₂ with alkali metal carbonates or acetates.

6. W and/or X=alkylsulfonyl, phenylsulfonyl or toluylsulfonyl

By reaction of compounds of the formula I in which W and/or X=—NO₂ with corresponding sulfinates, in particular alkali metal sulfinates.

7. W and/or X=alkoxy, phenoxy, toluyloxy, alkenyloxy or alkynyloxy

By reaction of compounds of the formula I in which W and/or X=—NO₂ with corresponding alcoholates or phenolates, in particular with alkali metal alcoholates or phenolates.

8. W and X=alkylthio, halogenoalkylthio, phenylthio, chlorophenylthio or toluylthio By reaction of compounds of the formula I in which W and/or X=—NO₂ with corresponding mercaptans or salts thereof, in particular alkali metal salts or quaternary ammonium salts.

9. W and/or X=1-nitroalkyl

By reaction of compounds of the formula I in which W and/or X=—NO₂ with nitroalkanes in the presence of a base, such as potassium carbonate, or with salts of nitroalkanes.

10. W and/or X=—CH(COOR₃)₂ or —C(COOR₃)(CH₃)

By reaction of compounds of the formula I in which W and/or X=—NO₂ with dimethyl or diethyl malonate or dimethyl or diethyl methylmalonate in the presence of a base, such as potassium carbonate, or by reaction of the said compounds with previously formed alkali metal salts of the said esters.

11. W and/or X=—CH(COOR₃)(CN) or —C(CN)(COOR₃)(CH₃)

By reaction of compounds of the formula I in which W and/or X=—NO₂ with methyl or ethyl cyanoacetate or methyl or ethyl methylcyanoacetate in the presence of a base, such as potassium carbonate, or by reaction of the said compounds with previously formed salts, in particular alkali metal salts, of the said cyanoacetates.

12. W and/or X=—CH₂COOH or —CH(CH₃)(COOH)

By hydrolysis of compounds obtained according to 10), in an aqueous medium in the presence of an acid, such as HCl or H₂SO₄. Any ester groups Y present are simultaneously hydrolysed.

13. W and/or X=azido (N₃)

By reaction of compounds of the formula I in which W and/or X=—NO₂ with alkali metal azides, such as sodium azide or potassium azide.

14. W and/or X=4,5-bis-(C₁₋₂-alkoxycarbonyl)-1,2,3-triazolyl

By reaction of azido compounds obtained according to (13) with dimethyl or diethyl acetylenedicarboxylate.

Finally, a cyano group X (or X' or X") can be converted into a —CO —alkyl group.

It is generally unnecessary to isolate the acid halides obtained according to (1) before any further reaction according to (2) and (3). Reactions (2), (4) to (11), (13) and (14) are advantageously carried out in an organic or aqueous-organic medium. Inert organic solvents are, depending on the reactants, for example: chlorinated or non-chlorinated aliphatic hydrocarbons, such as methylene chloride or chloroform; aliphatic or cyclic ethers, such as diethyl ether, di-isopropyl ether, dimethoxyethane, tetrahydrofuran and dioxane; alkyl esters of aliphatic monocarboxylic acids having a total of 2–8 C atoms, such as methyl, ethyl and n-butyl acetate, and ethyl and n-butyl butyrate; N,N-dialkylamides of aliphatic monocarboxylic acids having 1–3 C atoms in the acid moiety, such as N,N-dimethylformamide and N,N-dimethylacetamide; dialkylsulfoxides, such as dimethylsulfoxide and diethylsulfoxide; alkylnitriles having 1–4 C atoms in the alkyl moiety, such as acetonitrile, propionitrile and butyronitrile; and hexamethylphosphoric acid triamide and N-methylpyrrolidone.

An excess of the corresponding alcohol or thiol is advantageously used as the solvent for the preparation of an ester or thioester. The reaction of the free acids of the formula I with a compound HY₁ is advantageously carried out in the presence of an agent which detaches water, such as HCl gas or concentrated hydrochloric acid, if necessary with azeotropic removal of water.

The starting materials of the formulae III, IV, VI and VIII are known, or they can be prepared by methods known per se. Some of the starting compounds of the formula II are new. They can be obtained in a manner known per se, for example by a process which comprises reacting a compound of the formula IX

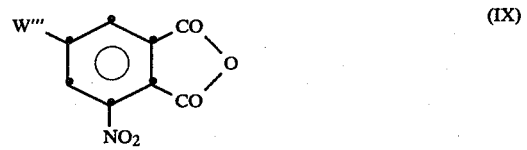

with a suitable amine or ammonia, for example a compound of the formula X

R—NH—Q‴ to give a compound of the formula XI

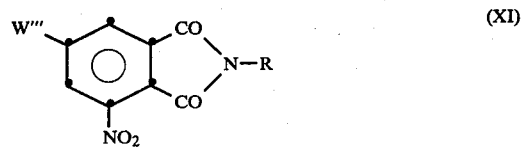

reacting the compound of the formula XI with a mercaptan of the formula XII

or a salt thereof, to give a compound of the formula XIII

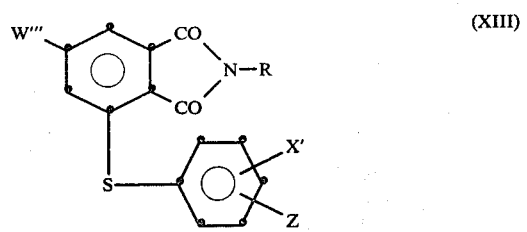

and hydrolysing the compound of the formula XIII to give a compound of the formula II. In the above formulae, W'''' is —NO$_2$, halogen, phenylsulfonyl, toluylsulfonyl, C$_{1-4}$-alkylsulfonyl, C$_{1-10}$-alkoxy, C$_{1-10}$-alkylthio, C$_{1-12}$-halogenoalkylthio, phenoxy, toluyloxy, phenylthio, chlorophenylthio, toluylthio, azido, C$_{3-5}$-alkenyloxy, C$_{3-5}$-alkinyloxy, 1-nitroalkyl having 1–5 C atoms, —CH$_2$COOH or —CH(CH$_3$)COOH, Q''' is hydrogen, —COH or —CONH-R, R is hydrogen, straight-chain or branched alkyl, in particular C$_{1-14}$-alkyl and especially methyl, or phenyl or toluyl, and X' and Z are as defined under formula II. If desired, a group W'''' can then be converted into a different group W'.

The compounds of the formula I according to the invention in which Y is other than —CO—halogen can be used as sensitizers for a wide variety of photo-crosslinkable polymers.

Such polymers are used, for example, for the production of printing plates for offset printing, for the production of photo-offset lacquers and for unconventional photography, for example for the production of photographic images by means of photo-polymerisation or photo-crosslinking. Such polymers are used, in particular, as so-called photo-resists for the production of printed circuits by methods known per se. The surface of the printed circuit board coated with the light-sensitive layer is exposed through a negative transparency of the conductive pattern and then developed, after which the unexposed areas of the layer are removed by developer liquid.

The polymers used are any materials of which the sensitivity to light (sensitivity towards actinic rays) can be increased by using the sensitisers according to the invention. The compounds of the formula I in which Y is other than —CO—halogen are especially suitable as sensitisers for polymers of the type described in German Offenlegungsschrift No. 2,626,769, i.e. polymers containing light-sensitive groups of the formula XIV

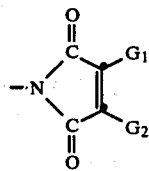
(XIV)

in which G$_1$ and G$_2$ independently of one another are alkyl having 1–4 C atoms, in particular methyl, or G$_1$ and G$_2$ together are the remaining members of a 5-membered to 6-membered carbocyclic ring.

The sensitisers according to the invention (Y is other than —CO—halogen) can be incorporated in a manner known per se into the photo-crosslinkable polymers. The sensitiser content of the polymer can vary greatly, depending on the field of use and the number of photo-crosslinkable groups which are present in the polymer, but is generally between about 0.1 and 20%, based on the weight of the polymer.

Finally, the compounds of the formula I in which Y is other than —CO—halogen can also be used as photoinitiators. The invention accordingly also relates to the use of the said compounds, together with amines, as initiators for photo-polymerisation of ethylenically unsaturated compounds or for photo-chemical crosslinking of polyolefins.

The organic amines used can be aliphatic, aromatic, araliphatic, cycloaliphatic or heterocyclic primary, secondary or tertiary amines. Examples are: butylamine, dibutylamine, tributylamine, cyclohexylamine, benzyldimethylamine, di-cyclohexylamine, triethylamine, phenyl-diethanolamine, piperidine, piperazine, morpholine, pyridine, quinoline, ethyl p-dimethylaminobenzoate or Michler's ketone [4,4'-bis-(dimethylamino)-benzophenone].

Mixtures of (A) a compound of the formula I in which X, Z, W and Y are as defined above as preferred and (B) an aliphatic tertiary amine, an alkyl p-dimethylaminobenzoate or Michler's ketone are preferred.

Examples of aliphatic tertiary amines are trimethylamine, triethylamine, tri-isopropyl-amine, tributylamine, dodecyl-dimethylamine, octyl-dimethylamine, triethanolamine, tris-(hydroxypropyl)-amine, N-methyl-diethanolamine or N-butyl-diethanolamine. Mixtures of (A) a compound of the formula I in which X, Y, Z and W are as defined above as preferred and (B) triethanolamine or a N-C$_{1-4}$-alkyldiethanolamine are particularly preferred.

The preferred mixtures mentioned preferably contain the compounds of the formula I in which Y is other than —CO—halogen and the organic amines in a weight ratio of 4:1 to 1:4.

Photo-polymerisable compounds are, for example, unsaturated monomers, such as esters of acrylic acid or methacrylic acid, for example methyl, ethyl, n- or tert.-butyl, isooctyl or hydroxyethyl acrylate, or methyl or ethyl methacrylate, 1,2-bis-(acrylyloxy)-ethane, 1,4-bis-(acrylyloxy)-butane, 1,6-bis-(acrylyloxy)-hexane, bis-(acrylyloxy)-neopentane, tris-acrylyl-trimethylolpropane, tetra-acrylyl-pentaerythritol or tris-acrylyl-pentaerythritol; acrylonitrile, methacrylonitrile, acrylamide, methacrylamide or N-substituted (meth)-acrylamides; vinyl esters, for example vinyl acetate, propionate, acrylate or succinate; other vinyl compounds, such as vinyl ethers, vinyl ketones, vinyl sulfones, styrene, alkylstyrenes, halogenostyrenes, divinylbenzene, N,N'-divinylurea, vinylnaphthalene, N-vinylpyrrolidone, vinyl chloride or vinylidene chloride; or allyl compounds, such as diallyl phthalate, diallyl maleate, triallyl isocyanurate, triallyl phosphate or ethylene glycol diallyl ether, and mixtures of these unsaturated monomers.

The mixtures according to the invention are particularly suitable for photo-polymerisation of the acrylates and mixtures thereof.

Further examples are unsaturated acrylic resins. These include, for example, reaction products of polyepoxides (epoxide resins) and acrylic acid or methacrylic acid, or reaction products of polyisocyanates and hydroxyalkyl acrylates, as well as reaction products of polyesters or polyethers containing hydroxyl groups and acrylic acid or methacrylic acid. These unsaturated acrylic resins are usually used as mixtures with one or more acrylates of a mono-, di- or poly-alcohol, for example ethyl, butyl, benzyl, 2-ethylhexyl, or 2-hydroxypropyl acrylate, 1,2-bis-(acrylyloxy)-ethane, 1,3-bis-(acrylyloxy)-propane, 1,4-bis-(acrylyloxy)-butane, 1,6-bis-(acrylyloxy)-hexane, tris-acrylyl-trimethylolpropane or tetra-acrylylpentaerythritol.

The invention also relates to photo-polymerisable systems consisting of (a) at least one ethylenically unsaturated compound, (b) a mixture of (A) and (B) of the type defined and, where relevant, (c) other additives, such as inhibitors, stabilisers, UV-absorbers, fillers, pigments, dyes, thixotropic agents and flow control agents, for example silicone oil.

The inhibitors used, which, in particular, should prevent premature polymerisation during preparation of the systems by mixing the components, are, for example, hydroquinone, hydroquinone derivatives, p-methoxyphenol or β-naphthols. UV-absorbers which can be used are, for example, those of the benzotriazole or benzophenone type. Fillers are, for example, silicic acid, talc or gypsum.

Preferred photo-polymerisable systems of this type are those containing 99.5–80% by weight of (a) and (c) and 0.5–20% by weight of (b), component (A) of mixture (b) preferably consisting of a compound of the formula I in which X, Z, Y and W are as defined above as preferred.

An acrylate or a mixture of several acrylates is oreferably used as component (a).

Combinations with known photo-initiators which form free radicals by photo-fragmentation, for example benzoin ethers, dialkoxyacetophenones or benzil ketals, can also be used.

The initiator mixtures according to the invention are of great importance for photo-curing of printing inks and pigmented white coatings, since the drying time of the binder is a decisive factor for the rate of production of graphic products and should be of the order of fractions of seconds. The initiators according to the invention are also particularly suitable for photo-curable systems for the production of printing plates.

Another field of use is UV-curing of coatings on metals, for example in the lacquering of metal sheets for tubes, cans or bottle closures, and the UV-curing of coatings on plastic, for example on floor or wall coverings based on PVC.

Examples of UV-curing of coatings on paper are colourless lacquering of labels, gramophone record sleeves and book jackets.

The mixtures according to the invention can also be used as initiators for photo-chemical crosslinking of polyolefins. Polyolefins in this context are, for example, polypropylene, polybutene, polyisobutylene and copolymers, for example ethylene/propylene copolymers, but preferably low, medium or high density polyethylene.

The photo-initiators are generally added to the photo-polymerisable systems by simply being stirred in, since most of these systems are liquid or readily soluble. In most cases, the initiators dissolve, whereby uniform distribution thereof and the transparency of the polymers is ensured.

Polymerisation is effected by known methods of photo-polymerisation by irradiation with light with a high content of short-wave radiation. Suitable sources of light are, for example, medium-pressure, high-pressure and low-pressure mercury lamps and super-actinic fluorescent tubes with emission maxima in the range between 250 and 450 nm.

In photo-chemical crosslinking of polyolefins, the photo-initiator is added to the polyolefin, for example by mixing in powder form or by mixing with the plasticised polyolefin, before or during the shaping processing. Crosslinking is effected by irradiating the shaped article in solid form, for example in the form of a film or fibres.

A. Preparation examples

EXAMPLE 1

3-Nitrothioxanthone-1-carboxylic acid (a) 116.2 g (0.364 mol) of 5-nitro-3-phenylthiophthalic acid and 2,440 g of polyphosphoric acid are stirred at 200° C. for 5 hours. After cooling, the mixture is poured onto ice/water (6 liters) and extracted by stirring for 2 hours, and the product is filtered off and dried. After recrystallisation from isopropanol (with active charcoal), 77.8 g (71% of theory) of 3-nitrothioxanthone-1-carboxylic acid are obtained; melting point: 245° C. (decomposition).

(b) 78.1 g (0.259 mol) of 5-nitro-3-phenylthiophthalic anhydride and 103.8 g (0.778 mol) of aluminium trichloride in 770 ml of 1,1,2,2-tetrachloroethane are warmed slowly to 110° C. and left at this temperature for 30 minutes. After cooling, the mixture is evaporated, the residue is stirred thoroughly with dilute hydrochloric acid and the product is filtered off and dried over $P_2O_5$ in vacuo. Yield: 77.3 g (99% of theory); melting point 248° C. (decomposition).

Analysis for $C_{14}H_7NO_5S$ (molecular weight: 301.27): calculated: C 55.82%, H 2.34%, N 4.65%, S 10.64%. found: C 56.1%, H 2.6%, N 4.7%, S 10.5%.

The 5-nitro-3-phenylthiophthalic acid used in the above example can be prepared as follows:

2 kg (8.4 mols) of 3,5-dinitrophthalic anhydride and 897 g (8.4 mols) of p-toluidine in 6.2 l of glacial acetic acid are kept under reflux for 3 hours. After cooling, the mixture is filtered, the residue is rinsed with 2 l of water and then suspended in 25 l of water, and the product is filtered off and dried at 100° C. in vacuo. 2,339 g (85% of theory) of N-(p-toluyl)-3,5-dinitrophthalimide are obtained; melting point: 182°–3° C.

820 mg (2.5 mmols) of N-(p-toluyl)-3,5-dinitrophthalimide, 0.33 g (3 mmols) of thiophenol and 29 mg (0.125 mmols; 5% by weight) of benzyltriethylammonium chloride are dissolved in 15 ml of $CH_2Cl_2$, after which a solution of 0.492 g (6 mmols) of anhydrous sodium acetate in 4 ml of water is added. After stirring the mixture vigorously at 25° C. for 20 minutes, it is diluted with water and adjusted to pH 9–10 and the organic phase is separated off, washed with 2 N NaOH, dried over sodium sulfate and evaporated. After recrystallising the residue from toluene, 930 mg (95% of theory) of N-(p-toluyl)-5-nitro-3-phenylthiophthalimide of melting point 207°–209° C. are obtained.

160 g (0.41 mol) of N-(p-toluyl)-5-nitro-3-phenylthiophthalimide in 1,590 ml of 20% sodium hydroxide solution are kept under reflux overnight, with stirring. The mixture is acidified with concentrated hydrochloric acid, whilst being cooled well (10°–15° C.), and the amide-acid is filtered off and stirred under reflux with 1,070 ml of concentrated hydrochloric acid for 3 hours. After cooling, the mixture is filtered, the residue is stirred into 650 ml of 5% $Na_2CO_3$ solution, the solid is filtered off and the filtrate is acidified. After cooling the mixture and filtering off the product and drying it in vacuo over phosphorus pentoxide, 116.2 g (89% of theory) of 5-nitro-3-phenylthiophthalic acid are obtained; melting point: 183°–5° C.

The 5-nitro-3-phenylthiophthalic anhydride can be prepared as follows:

4.3 g (13.5 mmols) of 5-nitro-3-phenylthiophthalic acid and 4.1 g (40.2 mmols) of acetic anhydride in 100 ml of toluene are kept under reflux for 1 hour. After evaporating the mixture and recrystallising the residue from methylene chloride/n-pentane, 3.97 g (98% of theory) of 5-nitro-3-phenylthiophthalic anhydride are obtained; melting point: 167°–9° C.

EXAMPLE 2

7-Methyl-3-nitrothioxanthone-1-carboxylic acid 12.7 g (40.3 mmols) of 3-(p-methylphenylthio)-5-nitrophthalic anhydride and 16.1 g (121 mmols) of aluminium trichloride in 120 ml of 1,1,2,2-tetrachloroethane are slowly heated to 120° C. After cooling, the mixture is evaporated, the residue is stirred in dilute hydrochloric acid and the product is filtered off and dried. After recrystallisation from isopropanol, 7.37 g (58% of theory of 7-methyl-3-nitrothioxanthone-1-carboxylic acid are obtained; melting point: >250° C.

Analysis for $C_{15}H_9NO_5S$ (molecular weight 315.30): calculated: C 57.14% H 2.88% N 4.44% S 10.17%. found: C 56.7% H 3.1% N 4.3% S 10.0%.

The 3-(p-methylphenylthio)-5-nitrophthalic anhydride used in the above example can be prepared as follows:

46.05 g (0.180 mol) of 3,5-dinitrophthalic acid and 26 g (0.25 mol) of acetic anhydride in 210 ml of toluene are kept under reflux for one hour. The mixture is filtered hot and the filtrate is evaporated. The residue is dissolved in 4.6 liters of methylene chloride under reflux, together with 27.4 g (0.221 mol) of p-thiocresol and 34.7 g (0.34 mol) of acetic anhydride. This solution is added dropwise to a solution of 1.9 g (8.5 mmols) of benzyltriethylammonium chloride in 190.4 g of 50% potassium hydroxide solution (1.7 mols) at 20°–27° C. with vigorous stirring. After the dropwise addition (135 minutes), the mixture is extracted by stirring for 90 minutes and is acidified with concentrated hydrochloric acid, with cooling. The mixture is converted into two clear phases by adding water and acetone; the organic phase is separated off, dried over sodium sulfate and evaporated. The residue is heated under reflux with 36.7 g of acetic anhydride in 200 ml of toluene, the mixture is filtered hot and the filtrate is evaporated. The above reaction is repeated with the residue, using 21.8 g (0.214 mol) of acetic anhydride, 19.9 g (0.161 mol) of p-thiocresol, 2.4 g of benzyltriethylammonium chloride and 285 g of 30% NaOH solution. After the extraction by stirring, the mixture is acidified and the organic phase is separated off, dried over sodium sulfate and evaporated. The residue is converted into the anhydride with 52.1 g of acetic anhydride and 250 ml of toluene. After recrystallisation from methylene chloride/n-pentane, 20.83 g (39% of theory) of 3-(p-methylphenylthio)-5-nitrophthalic anhydride are obtained; melting point: 180°–2° C.

EXAMPLE 3

7-Methoxy-3-nitrothioxanthone-1-carboxylic acid 2.4 g (7.25 mmols) of 3-(p-methoxyphenylthio)-5-nitrophthalic anhydride and 2.9 g (21.75 mmols) of aluminium trichloride in 24 ml of 1,1,2,2-tetrachloroethane are heated slowly to 120° C. After cooling, the mixture is evaporated and the residue is stirred thoroughly in dilute hydrochloric acid. The product is filtered off, dried, and recrystallised from isopropanol. 648 mg (27% of theory) of 7-methoxy-3-nitrothioxanthone-1-carboxylic acid are obtained; melting point: 268° C.

Analysis for $C_{15}H_9NO_6S$ (molecular weight 331.30): calculated: C 54.38% H 2.74% N 4.23% S 9.68%. found: C 54.1% H 3.0% N 4.1% S 9.8%.

The 3-(p-methoxyphenylthio)-5-nitrophthalic anhydride used in the above example can be prepared as follows:

12.17 g (51.1 mmols) of 3,5-dinitrophthalic anhydride are dissolved in 1,350 ml of methylene chloride, after which 10.7 g (76.6 mmols) of 4-methoxythiophenol and 10.2 g (100 mmols) of acetic anhydride are added. This solution is added dropwise to a mixture of 1.2 g of benzyltriethylammonium chloride, 68.6 g of 33% KOH solution (408 mmols) and 50 ml of methylene chloride at 20°–24° C., with vigorous stirring. After 2 hours, the mixture is acidified with hydrochloric acid and extracted with methylene chloride, and the product phase is dried over sodium sulfate and evaporated. The residue is converted into the anhydride with 5.3 g of acetic anhydride in 100 ml of toluene under reflux. The solution is filtered hot and the mother liquor is evaporated. The dark residue is boiled up several times with cyclohexane. After evaporating the mixture, 5.15 g (31% of theory) of 3-(p-methoxyphenylthio)-5-nitrophthalic anhydride are obtained; melting point: 143°–148° C.

EXAMPLE 4

6,7-Dichloro-3-nitrothioxanthone-1-carboxylic acid (A) and 7,8-dichloro-3-nitrothioxanthone-1-carboxylic acid (B)

11.66 g (31.5 mmols) of 3-(3,4-dichlorophenylthio)-5-nitrophthalic anhydride and 8.38 g (63 mmols) of aluminium trichloride in 120 ml of 1,1,2,2-tetrachloroethane are warmed to 100° C. overnight and the mixture is then cooled and evaporated. The residue is shaken with 200 ml of 2 N hydrochloric acid and 200 ml of tetrahydrofuran. 200 ml of toluene are then added and the organic phase is separated off, washed with saturated NaCl solution, dried over sodium sulfate and evaporated. 7.17 g (61% of theory) of 6,7-dichloro-3-nitrothioxanthone-1-carboxylic acid (A) are obtained by recrystallisation of the residue from ethyl acetate/toluene; melting point: 253°–5° C. (decomposition).

Analysis for $C_{14}H_5Cl_2NO_5S$ (molecular weight 370.16): calculated: C 45.43% H 1.36% N 3.78%. found: C 45.53% H 1.45% N 3.97%.

620 mg (5% of theory) of 7,8-dichloro-3-nitrothioxanthone-1-carboxylic acid (B) are isolated from the mother liquor; melting point: 250° C. (decomposition). Analysis: found C 45.35% H 1.67% N 3.83%.

The 3-(3,4-dichlorophenylthio)-5-nitrophthalic anhydride used in the above example can be prepared as follows:

238.11 g (1 mol) of 3,5-dinitrophthalic anhydride are dissolved in one liter of xylene under reflux. 62.02 g (1.05 mol) of N-methylformamide are added dropwise under reflux in the course of 30 minutes. After 18 hours under reflux, the water formed and the formic acid are distilled off, together with a little xylene (total: 140 ml), during which the boiling point rises to 137° C. The solution is filtered hot. After slowly cooling and concentrating the mother liquor, 209.42 g (83% of theory) of 3,5-dinitrophthalic acid N-methylimide are obtained; melting point: 174°–6° C.

18.84 g (75 mmols) of 3,5-dinitrophthalic acid N-methylimide are introduced into 250 ml of ethyl acetate and the mixture is treated with 30.4 g (220 mmols) of ground, anhydrous potassium carbonate, after which 14 g (78 mmols) of 3,4-dichlorothiophenol are added dropwise. After adding 95 ml of tetrahydrofuran, the mixture is stirred overnight and then evaporated to dryness. The residue is kept with 100 ml of water under reflux overnight, the mixture is extracted with petroleum ether at 25° C. and the extract is filtered, and the aqueous filtrate is acidified with 300 ml of 2 N HCl and heated under reflux. After 2.5 hours, the mixture is cooled and extracted with tetrahydrofuran/toluene, and the extract is washed with saturated NaCl solution, dried over sodium sulfate and evaporated. The residue is warmed under reflux with 100 ml of toluene and 7.66 g (75 mmols) of acetic anhydride and, after cooling, the mixture is evaporated. After recrystallisation of the residue from methylene chloride/n-pentane, 22.2 g (80% of theory) of 3-(3,4-dichlorophenylthio)-5-nitrophthalic anhydride are obtained; melting point: 154°–7° C.

EXAMPLE 5 n-Butyl 7-methyl-3-nitrothioxanthone-1-carboxylate 3.2 g (10.15 mmols) of 7-methyl-3-nitrothioxanthone-1-carboxylic acid [prepared according to Example 2] and 20 ml of oxalyl chloride are kept under reflux for 5 hours. After evaporating the mixture, 20 ml of n-butanol are added dropwise to the residue, with ice-cooling, and the mixture is warmed under reflux for 30 minutes. After concentrating the mixture and recrystallising the residue from toluene/cyclohexane, 2.7 g (72% of theory) of n-butyl 7-methyl-3-nitrothioxanthone-1-carboxylate are obtained; melting point: 164°–7° C.

Analysis for $C_{19}H_{17}NO_5S$ (molecular weight 371.41): calculated: C 61.45% H 4.62% N 3.77% S 8.63%. found: C 60.40% H 4.40% N 3.95% S 8.60%.

EXAMPLE 6

7-Methyl-3-nitrothioxanthone-1-carboxylic acid N-n-butylamide 1 g (3.17 mmols) of 7-methyl-3-nitrothioxanthone-1-carboxylic acid is suspended in 15 ml of methylene chloride. 2 drops of pyridine are then added, and 0.56 g (4.76 mmols) of thionyl chloride is added dropwise. After keeping the mixture under reflux for 2 hours, the clear solution is concentrated and 5 ml of benzene are added to the residue. A solution of 0.7 g (951 mmols) of n-butylamine in benzene is then added dropwise. After stirring at 25° C. for 30 minutes, the mixture is concentrated, the residue is taken up in methylene chloride/water and the organic phase is dried over sodium sulfate and evaporated. After recrystallising the residue from methylene chloride/n-pentane, 0.68 g of 7-methyl-3-nitrothioxanthone-1-carboxylic acid N-n-butylamide (58% of theory) is obtained; melting point >250° C.

Analysis for $C_{19}H_{18}N_2O_4S$ (molecular weight 370.42): calculated: C 61.61% H 4.90% N 7.56% S 8.66%. found: C 61.2% H 5.3% N 7.2% S 8.3%.

EXAMPLE 7

7-Methoxy-3-nitrothioxanthone-1-carboxylic acid N,N-di-n-butylamide 100 g (0.302 mmol) of 7-methoxy-3-nitrothioxanthone-1-carboxylic acid are suspended in 1.5 ml of methylene chloride. 1 drop of pyridine and 54 mg (0.453 mmol) of thionyl chloride are then added. After 1 hour at 25° C., the clear solution is evaporated and the residue is treated with 117 mg (0.906 mmol) of di-n-butylamine in 10 ml of benzene. After 35 minutes at 25° C., the mixture is evaporated and the residue is taken up in methylene chloride/water. The organic phase is dried over sodium sulfate and concentrated. Recrystallisation of the residue from methanol/water gives 109 mg (82% of theory) of 7-methoxy-3-nitrothioxanthone-1-carboxylic acid N,N-di-n-butylamide; melting point: 130°–33° C.

Analysis for $C_{23}H_{26}N_2O_5S$ (molecular weight 442.53): calculated: C 62.43% H 5.92% N 6.33% S 7.25%. found: C 61.9% H 5.9% N 6.0% S 7.0%.

EXAMPLE 8

3-Chlorothioxanthone-1-carboxylic acid 3 g (9.96 mmols) of 3-nitrothioxanthone-1-carboxylic acid and 20 ml of thionyl chloride are kept under reflux for 2 days. The mixture is concentrated and the residue is kept with water under reflux for 30 minutes. After cooling, the mixture is filtered, the residue is dissolved in tetrahydrofuran/toluene and the solution is dried with sodium sulfate and evaporated. After drying the residue at 120° C. in vacuo, 2.65 g (92% of theory) of 3-chlorothoxanthone-1-carboxylic acid are obtained; melting point: 268°–71° C.

Analysis for $C_{14}H_7ClO_3S$ (molecular weight 290.72): calculated: C 57.84% H 2.43% S 11.03% Cl 12.20%. found: C 57.5% H 2.6% S 10.8% Cl 11.50%.

EXAMPLE 9

Ethyl 3-chlorothioxanthone-1-carboxylate 1 g (3.32 mmols) of 3-nitrothoxanthone-1-carboxylic acid and 10 ml of thionyl chloride are kept under reflux for 2 days. The mixture is evaporated and the residue is kept with 10 ml of absolute ethanol under reflux for 1 hour. After evaporating the mixture and recrystallising the residue from ethanol/acetonitrile, 0.82 g (77% of theory) of ethyl 3-chlorothioxanthone-1-carboxylate is obtained; melting point: 133°–5° C.

Analysis for $C_{16}H_{11}ClO_3S$ (molecular weight 318.77): calculated: C 60.29% H 3.48% S 10.06% Cl 11.12%. found: C 60.2% H 3.4% S 10.0% Cl 11.2%.

EXAMPLE 10 n-Octyl 3-chlorothioxanthone-1-carboxylate n-Octyl 3-chlorothioxanthone-1-carboxylate is prepared in a manner analogous to that described in Example 9. Yield (after recrystallisation from petroleum ether): 0.27 g (20% of theory); melting point: 63°–5° C.

Analysis for $C_{22}H_{23}ClO_3S$ (molecular weight 402.94): calculated: C 65.58% H 5.76% S 7.96% Cl 8.80%. found: C 65.1% H 5.8% S 8.0% Cl 8.7%.

EXAMPLE 11

3-Chlorothioxanthone-1-carboxylic acid nitrile 2.1 g (6.58 mmols) of 3-nitrothioxanthone-1-carboxylic acid and 20 ml of thionyl chloride are kept under reflux for 2 days and the mixture is then evaporated. The residue is stirred with 10 ml of a 25% solution of ammonia in water for 5 hours and the precipitate is filtered off. The treatment with thionyl chloride and ammonia solution is repeated three times. The residue is washed with 1 N sodium hydroxide solution and water, dried thoroughly and kept with 10 ml of thionyl chloride under reflux for one day. After evaporating the mixture, the residue is washed with water and chromatographed over silica gel using methylene chloride. Recrystallisation of the product from methylene chloride/n-pentane gives 330 mg (19% of theory) of 3-chlorothioxanthone-1-carboxylic acid nitrile; melting point: 263°–4° C.

Analysis for $C_{14}H_6ClNOS$ (molecular weight 271.72): calculated: C 61.89% H 2.23% N 5.16% S 11.80% Cl 13.05%. found: C 60.9% H 2.4% N 5.1% S 11.8% Cl 14.0%.

EXAMPLE 12 n-Butyl 3-Bromothioxanthone-1-carboxylate 602 mg (2 mmols) of 3-nitrothioxanthone-1-carboxylate and 17 g (62.8 mmols) of phosphorus tribromide are stirred at 110° C. overnight. The mixture is carefully treated with 20 ml of n-butanol, with ice-cooling, and is kept under reflux for 30 minutes and evaporated. The residue is stirred with saturated $NaHCO_3$ solution for one hour, the mixture is extracted with methylene chloride and the extracts are washed with saturated NaCl solution, dried over $Na_2SO_4$ and evaporated. After chromatography of the residue using methylene chloride/silica gel, 160 mg (20% of theory) of n-butyl 3-bromothioxanthone-1-carboxylate are obtained; melting point: 117°–120° C.

Analysis for $C_{18}H_{15}BrO_3S$ (molecular weight 391.28): calculated: C 55.26% H 3.87% Br 20.42%. found: C 54.72% H 3.78% Br 19.17%.

EXAMPLE 13

Methyl 3-nitrothioxanthone-1-carboxylate 40.3 g (0.13 mol) of 3-nitrothioxanthone-1-carboxylic acid are suspended in 1,400 ml of methanol. Dry hydrogen chloride gas is then passed into this suspension at 5°–10° C. in the course of 8 hours. The resulting brown suspension is then boiled under reflux under a weak stream of hydrogen chloride gas for 12 hours. The reaction mixture is then poured gradually into 3 liters of water, during which the pH value of the water is continuously kept at 7–8 by adding solid sodium bicarbonate. The suspension obtained is filtered, and the product phase is dried over phosphorus pentoxide at 80° C. The resulting crude product is twice subjected to extraction, with 150 ml of toluene each time, and filtration. The combined toluene solutions are filtered over 40 g of aluminium oxide. 26.6 g (65% of theory) of methyl 3-nitrothioxanthone-1-carboxylate crystallise out; melting point: 197° C.

The insoluble residue obtained in the extraction with toluene consists of 3-nitrothioxanthone-1-carboxylic acid, which can be re-used. IR spectrum (KBr): 1750 $cm^{-1}$ (—COOR); 1655 $cm^{-1}$ (—CO—). UV spectrum: $\lambda_{max}=411$ nm, $\epsilon=4350$.

Analysis for $C_{15}H_9NO_5S$ (molecular weight: 315.30): calculated: C 57.14% H 2.88% N 4.44% S 10.17%. found: C 57.16% H 2.83% N 4.41% S 10.10%.

EXAMPLE 14

Methyl 3-aminothioxanthone-1-carboxylate 4 g (0.0126 mol) of methyl 3-nitrothioxanthone-1-carboxylate are dissolved in 40 ml of dioxane and hydrogenated at 25° C. in the presence of 2 g of a Pd-on-charcoal catalyst (5% by weight of Pd). The resulting suspension is filtered and the residue is boiled up three times with in each case 50 ml of dioxane. The combined dioxane solutions are evaporated to dryness in a rotary evaporator. 3.4 g (94.4% of theory) of methyl 3-aminothioxanthone-1-carboxylate are obtained; melting point >250° C. IR spectrum (KBr): 1750 $cm^{-1}$ (—COOR); 1645 $cm^{-1}$ (—CO—). UV spectrum: $\lambda_{max}=353$ nm, $\epsilon=12780$.

Analysis for $C_{15}H_{11}NO_3S$ (molecular weight 285.32): calculated: C 63.15% H 3.89% N 4.91% S 11.24%. found: C 63.50% H 3.70% N 4.75% S 10.94%.

EXAMPLE 15

Methyl 3-N,N-dimethylaminothioxanthone-1-carboxylate 1.23 g (0.0431 mol) of methyl 3-aminothioxanthone-1-carboxylate, 0.53 ml of 35% aqueous formaldehyde solution and 0.65 ml of formic acid are heated under reflux for 12 hours. The reaction mixture is evaporated to dryness and the residue is stirred with 3 ml of water and then with 5 ml of methanol and dried. 1.19 g (71.7% of theory) of methyl 3-N,N-dimethylaminothioxanthone-1-carboxylate are obtained; melting point: 146° C. IR spectrum (dioxane): 1745 $cm^{-1}$ (—COOR); 1645 $cm^{-1}$ (—CO—). UV spectrum: $\lambda_{max}=368$ nm $\epsilon=11700$.

Analysis for $C_{17}H_{15}NO_3S$ (molecular weight 313.37): calculated: C 65.16% H 4.83% N 4.47% S 10.23%. found: C 65.45% H 4.98% N 4.36% S 9.90%.

EXAMPLE 16

Methyl 3-Methoxythioxanthone-1-carboxylate 2 g (6.35 mmols) of methyl 3-nitrothioxanthone-1-carboxylate, 9.53 ml of a 1.0 M sodium methylate solution in methanol (9.53 mmols) and 10 ml of absolute methanol are kept under reflux for 1 hour, the mixture is evaporated with toluene, the residue is dissolved in methylene chloride and the solution is dried over sodium sulfate and evaporated. Recrystallisation of the residue from methylene chloride/n-pentane gives 1.64 g (86% of theory) of methyl 3-methoxythioxanthone-1-carboxylate; melting point: 163°–65° C.

Analysis for $C_{15}H_{12}O_4S$ (molecular weight 288.32): calculated: C 62.49% H 4.20% S 11.12%. found: C 62.75% H 4.07% S 11.01%.

EXAMPLE 17

Methyl 3-(p-chlorophenylthio)-thioxanthone-1-carboxylate 1 g (3.17 mmols) of methyl 3-nitrothioxanthone-1-carboxylate, 0.55 g (3.81 mmols) of p-chlorothiophenol and 1.6 g (11.42 mmols) of ground, anhydrous potassium carbonate in 10 ml of N,N-dimethylformamide at 25° C. for 2 hours. The mixture is evaporated and the residue is taken up in methylene chloride/water. The organic phase is dried over sodium sulfate and evaporated. Recrystallisation of the residue from toluene gives 1.02 g (78% of theory) of methyl 3-p-chlorophenylthio-thioxanthone-1-carboxylate; melting point: 169°–70° C.

Analysis for $C_{21}H_{13}ClO_3S_2$ (molecular weight 412.91): calculated C 61.09% H 3.18% S 15.53% Cl 8.59%. found C 61.2% H 3.1% S 15.5% Cl 8.6%.

EXAMPLE 18

Methyl 3-(2-nitro-2-n-propyl)-thioxanthone-1-carboxylate 630 mg (2 mmols) of methyl 3-nitrothioxanthone-1-carboxylate and 535 mg (6 mmols) of 2-nitropropane are dissolved in 4 ml of N,N-dimethylformamide at 80° C., and 1.66 g (12 mmols) of ground, anhydrous potassium carbonate are added. After 2 hours, the mixture is evaporated, the residue is taken up in methylene chloride/- water and the organic phase is dried over sodium sulfate and concentrated. Recrystallisation of the residue from methylene chloride/n-pentane gives 580 mg (81% of theory) of methyl 3-(2-nitro-2-n-propyl)-thioxanthone-1-carboxylate; melting point: 208°–210° C. (decomposition).

Analysis for $C_{18}H_5NO_5S$ (molecular weight 357.38): calculated C 60.50% H 4.23% N 3.92% S 8.97%. found C 60.45% H 4.27% N 3.92% S 8.75%.

EXAMPLE 19

Methyl 3-bis-(methoxycarbonylmethyl)-thioxanthone-1-carboxylate 630 mg (2 mmols) of methyl 3-nitrothioxanthone-1-carboxylate, 793 mg (6 mmols) of dimethyl malonate and 1.66 g (12 mmols) of anhydrous potassium carbonate are stirred in 4 ml of N,N-dimethylformamide at 80° C. for 1.5 hours. After evaporating the mixture, the residue is taken up in methylene chloride/water and the organic phase is washed with saturated sodium bicarbonate solution, dried over sodium sulfate and evaporated. Recrystallisation of the residue from methylene chloride/diethyl ether gives 720 mg (90% of theory) of methyl 3-bis-methoxycarbonylmethyl-thioxanthone-1-carboxylate; melting point: 145°–8° C.

Analysis for $C_{20}H_{16}O_7S$ (molecular weight 400.40): calculated C 60.00% H 4.03% S 8.01%. found C 60.29% H 4.28% S 7.86%.

EXAMPLE 20

3-Carboxymethyl-thioxanthone-1-carboxylic acid 4.00 g (10 mmols) of methyl 3-bis-methoxycarbonylmethyl-thioxanthone-1-carboxylate in a mixture of 20 ml of 96% sulfuric acid and 40 ml of water are stirred under reflux for three days and the mixture is cooled, and diluted with 20 ml of water. 200 ml of tetrahydrofuran are then added, and 200 ml of toluene are added to the clear solution. After extracting the mixture by shaking, the organic phase is washed with acid, saturated sodium chloride solution, all the aqueous extracts are re-extracted, and the organic phases are dried over sodium sulfate and evaporated. Recrystallisation of the residue from tetrahydrofuran gives 2.84 g (90% of theory) of 3-carboxymethylthioxanthone-1-carboxylic acid; melting point <250° C. (decomposition).

Analysis for $C_{16}H_{10}O_5S$ (molecular weight 314.31): calculated C 61.14% H 3.21% S 10.20%. found: C 61.30 % H 3.50 % S 10.11 %.

EXAMPLE 21

Ethyl 3-nitrothioxanthone-1-carboxylate (a) 10 g (33.2 mmols) of 3-nitrothioxanthone-1-carboxylic acid, 0.5 g of p-toluenesulfonic acid.H2O, 50 ml of ethanol and 100 ml of toluene are heated under reflux, the refluxing solvent mixture being freed from the water with 15 g of a 3 Å molecular sieve. After 2 days, the mixture is evaporated, the residue is taken up in methylene chloride and the mixture is filtered. The mother liquor is chromatographed over 100 g of silica gel using methylene chloride. 4.3 (39% of theory) of ethyl 3-nitrothioxanthone-1-carboxylate are obtained; melting point: 174°–5° C.

(b) 30.8 g (102.3 mmols) of 3-nitrothioxanthone-1-carboxylic acid and 150 ml of thionyl chloride are kept under reflux for 30 minutes, the mixture is evaporated and 260 ml of absolute ethanol are added to the residue at 15°–30° C. After 10 minutes under reflux, the mixture is concentrated, the residue is dissolved in a little methylene chloride and the solution is chromatographed over 200 g of silica gel using methylene chloride. 22.45 g (67% of theory) of ethyl 3-nitrothioxanthone-1-carboxylate are obtained; melting point: 172°–3° C.

Analysis for $C_{16}H_{11}NO_5S$ (molecular weight 329.33): calculated: C 58.36% H 3.37% N 4.26% S 9.74%. found: C 57.9% H 3.6% N 4.5% S 9.9%.

EXAMPLE 22

Ethyl 3-ethoxythioxanthone-1-carboxylate 5.0 g (15.2 mmols) of ethyl 3-nitrothioxanthone-1-carboxylate in 40.0 ml of a 0.50 N solution of sodium ethylate in absolute ethanol are kept under reflux overnight. After evaporating the mixture, the residue is taken up in methylene chloride/2 N HCl solution and the organic phase is dried with sodium sulfate and evaporated. Crystallisation of the residue from methylene chloride/n-pentane gives 3.21 g (64% of theory) of ethyl 3-ethoxythioxanthone-1-carboxylate; melting point: 158°–160° C.

Analysis for $C_{18}H_{16}O_4S$ (molecular weight 328.38): calculated: C 65.84% H 4.91% S 9.76%. found: C 65.84% H 5.02% S 9.71%.

EXAMPLE 23

Ethyl 3-methylsulfonylthioxanthone-1-carboxylate 2 g (6.08 mmols) of ethyl 3-nitrothioxanthone-1-carboxylate and 1.245 g (12.2 mmols) of sodium methylsulfonate in 15 ml of N,N-dimethylformamide are kept at 80° C. for 3 hours. After evaporating the mixture, the residue is taken up in methylene chloride/water and the organic phase is washed with water, dried over sodium sulfate and evaporated. After recrystallising the residue from toluene, 1.9 g of ethyl 3-methylsulfonylthioxanthone-1-carboxylate are obtained; melting point: 184°–6° C.

Analysis for $C_{17}H_{14}O_5S_2$ (molecular weight 362.41): calculated: C 56.34% H 3.90% S 17.69%. found: C 56.6% H 3.9% S 17.8%.

EXAMPLE 24

Ethyl 3-phenylsulfonylthioxanthone-1-carboxylate 6.6 g (20 mmols) of ethyl 3-nitrothioxanthone-1-carboxylate and 6.5 g (40 mmols) of sodium benzenesulfonate are stirred in 30 ml of N,N-dimethylformamide at 120° C. for 14 hours. After evaporating the mixture, the residue is washed with water and taken up in methylene chloride and the methylene chloride mixture is dried over sodium sulfate and evaporated. Recrystallisation of the residue from toluene gives 4.2 g (50% of theory) of ethyl 3-phenylsulfonylthioxanthone-1-carboxylate; melting point: 211°–213° C.

Analysis for $C_{22}H_{16}O_5S_2$ (molecular weight 424.49): calculated: C 62.25% H 3.80% S 15.11%. found: C 62.4% H 4.0% S 14.9%.

EXAMPLE 25

Ethyl 3-azidothioxanthone-1-carboxylate 3 g (9.1 mmols) of ethyl 3-nitrothioxanthone-1-carboxylate and 0.9 g of sodium azide are stirred in 20 ml of N,N-dimethylformamide at 80° C. for 1 hour. After evaporating the mixture at 50° C., the residue is washed with water and taken up in methylene chloride, after which the solution is dried over sodium sulfate, and the solution is evaporated and the residue dried at a maximum temperature of 50° C. 3.3 g (quantitative) of ethyl 3-azidothioxanthone-1-carboxylate are obtained; melting point: 154°–6° C. (decomposition). IR spectrum: 2210 cm$^{-1}$ (—N$_3$).

EXAMPLE 26

Ethyl 3-[4,5-bis-(methoxycarbonyl)-1,2,3-triazol-1-yl]-thioxanthone-1-carboxylate 1.1 g (3.08 mmols) of the azido compound according to Example 25, 4 g (33.9 mmols) of dimethyl acetylenedicarboxylate and 5 ml of ethyl acetate are stirred at 80° C. for 4 hours. After evaporating the mixture and recrystallising the residue from methylene chloride/n-pentane, 1.2 g (83% of theory) of the above thioxanthone are obtained; melting point: 198°–9° C.

Analysis for $C_{22}H_{17}N_3O_7S$ (molecular weight 467.45): calculated: C 56.53% H 3.66% N 8.99% S 6.86%. found: C 56.2% H 3.6% N 9.1% S 6.8%.

EXAMPLE 27

Ethyl 3-aminothioxanthone-1-carboxylate 3 g (9.12 mmols) of ethyl 3-nitrothioxanthone-1-carboxylate are hydrogenated in 60 ml of N,N-dimethylformamide under normal pressure and at 25° C. for 4 hours, using 0.9 g of a palladium-on-charcoal catalyst (5% by weight of Pd). After filtering the mixture and evaporating the filtrate, 2.7 g (100% of theory) of ethyl 3-aminothioxanthone-1-carboxylate are obtained; melting point >250° C. (decomposition from 205° C.).

Analysis for $C_{16}H_{13}NO_3S$ (molecular weight 299.34): calculated: C 64.20% H 4.38% N 4.68% S 10.71%. found: C 63.60% H 4.45% N 4.55% S 10.30%.

EXAMPLE 28

Ethyl 3-[2,2-bis-(ethoxycarbonyl)-ethyl]-thioxanthone-1-carboxylate 5 g (15.2 mmols) of ethyl 3-nitrothioxanthone-1-carboxylate, 10.6 g (60.8 mmols) of diethyl methylmalonate and 8.4 g (60.8 mmols) of potassium carbonate in 20 ml of N,N-dimethylformamide are stirred at 80° C. overnight. After evaporating the mixture, the residue is dissolved in methylene chloride/water and the organic phase is washed with sodium bicarbonate solution, dried over sodium sulfate and evaporated. After filtering the residue with methylene chloride over 5 g of silica gel and evaporating the filtrate and recrystallising the residue from diethyl ether, 4.66 g (67% of theory) of the above thioxanthone are obtained; melting point: 118°–9° C.

Analysis for $C_{24}H_{24}O_7S$ (molecular weight 456.51): calculated: C 63.14% H 5.30% S 7.02%. found: C 63.46% H 5.41% S 6.92%.

EXAMPLE 29

3-(2-Carboxyethyl)-thioxanthone-1-carboxylic acid 4.91 g (10.75 mmols) of the thioxanthone prepared in Example 28 are stirred in a mixture of 20 ml of 96% sulfuric acid and 30 ml of water under reflux overnight. The mixture is diluted with 100 ml of water and shaken with 100 ml of tetrahydrofuran until a solution is obtained, and 100 ml of toluene are then added. After shaking the mixture, the organic phase is separated off, the aqueous phase is re-extracted and the organic phases are washed with saturated acid sodium chloride solution, dried over sodium sulfate and evaporated. Recrystallisation of the residue from tetrahydrofuran/toluene gives 3.41 g (96% of theory) of the above thioxanthone; melting point 232°–6° C.

Analysis for $C_{17}H_{12}O_5S$ (molecular weight 328.34): calculated: C 62.19% H 3.69% S 9.77%. found: C 61.9% H 3.6% S 9.5%.

EXAMPLE 30

Methyl 3-(methoxycarbonyl-cyanomethyl)-thioxanthone-1-carboxylate 630 mg (2 mmols) of methyl 3-nitrothioxanthone-1-carboxylate, 396 mg (4 mmols) of methyl cyanoacetate, 1.11 g (8 mmols) of potassium carbonate and 4 ml of N,N-dimethylformamide are stirred at 70° C. for 10 minutes. The mixture is evaporated, the residue is taken up in 0.5 M HCl/methylene chloride/acetone and the organic phases are dried over Na$_2$SO$_4$ and evaporated. The crystallisation of the residue from methylene chloride gives 250 mg (34% of theory) of methyl 3-(metoxycarbonylcyanomethyl)-thioxanthone-1-carboxylate; melting point: 200°–205° C. (decomposition).

Analysis for $C_{19}H_{13}NO_5S$ (molecular weight 367.38): calculated: C 62.12% H 3.57% N 3.81% S 8.73%. found: C 62.35% H 3.25% N 3.89% S 8.68%.

EXAMPLE 31

3-(2-Hydroxyethylthio)-thioxanthone-1-carboxylic acid 15.06 g (50 mmols) of 3-nitrothioxanthone-1-carboxylic acid, 4.69 g (60 mmols) of 2-mercaptoethanol, 20.73 g (150 mmols) of potassium carbonate and 150 ml of dimethylformamide are stirred at 100° C. for 2 hours and the mixture is then evaporated to dryness. The residue is dissolved in 2 N sodium carbonate solution and extracted with tetrahydrofuran/toluene. The aqueous phase is acidified. After filtering off the precipitate and recrystallising it from dioxane, 11.05 g (67% of theory) of 3-(2-hydroxyethylthio)-thioxanthone-1-carboxylic acid of melting point 246°–249° C. are obtained.

Analysis for $C_{16}H_{12}O_4S_2$ (molecular weight 332.39): calculated: C 57.82% H 3.64% S 19.29%. found: C 57.65% H 3.75% S 19.00%.

EXAMPLE 32

Ethyl 3-(2-carboxyphenylthio)-thioxanthone-1-carboxylate 10 g (30.30 mmols) of ethyl 3-nitrothioxanthone-1-carboxylate [prepared according to Example 21], 9.06 g (45.73 mmols) of disodium thiosalicylate and 50 ml of dimethylformamide are stirred at 25° C. for 30 minutes, the mixture is evaporated and the residue is taken up in a mixture of 2 N HCl/tetrahydrofuran/toluene. The organic phase is dried with sodium sulfate and evaporated. Recrystallisation of the residue from toluene gives 11.66 g (88% of theory) of ethyl 3-(2-carboxyphenylthio)-thioxanthone-1-carboxylate; melting point: 207°–209° C.

Analysis for $C_{23}H_{16}O_5S_2$ (molecular weight 436.50): calculated: C 63.29% H 3.69% O 18.33% S 14.69%. found: C 63.20% H 3.70% O 18.40% S 14.20%.

B. Use examples

Example 1

(a) Preparation of the polymer

Polymers having the following structure and composition are prepared:

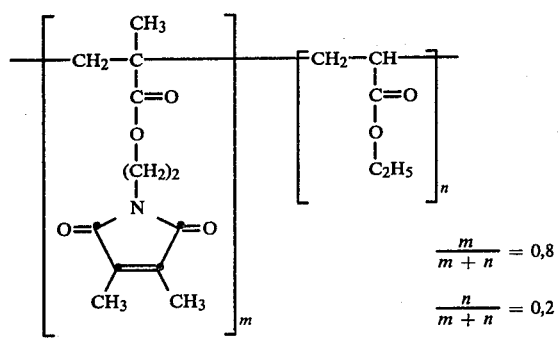

$$\frac{m}{m+n} = 0{,}8$$

$$\frac{n}{m+n} = 0{,}2$$

465.5 g (1.963 mols) of β-(dimethylmaleimidyl)ethyl methacrylate [prepared according to German Offenlegungsschrift 2,626,769] together with 49.15 g (0.49 mol) of ethyl acrylate are dissolved in 960 ml of 1-acetoxy-2-ethoxyethane under nitrogen. A solution of 3.86 g of azoisobutyronitrile in 25 ml of 1-acetoxy-2-ethoxyethane is allowed to run in at 80° C., under a nitrogen atmosphere, and polymerisation is then carried out for 6 hours. The still hot solution is stabilised with 2.57 g of 2,6-di-tert.-butyl-p-cresol. The mean molecular weight of the polymers thus obtained (determined by light scattering measurement in CHCl$_3$) and their limiting viscosity $\eta_{limit}$ are given in Table I which follows:

TABLE I

| | polymers used | | |
|---|---|---|---|
| Polymer No. | Mean molecular weight (light scattering measurement in CHCl$_3$) | dl/g | $\eta_{limit}$ in CHCl$_3$ |
| 1 | 10$^6$ | 0.43 | 20° C. |
| 2 | 4.36 × 10$^5$ | 0.29 | 20° C. |
| 3 | 1.5 × 10$^6$ | 0.475 | 20° C. |
| 4 | 1.51 × 10$^5$ | 0.156 | 25° C. |

(b) Production of images

The amounts of sensitiser indicated in Tables II to V which follow are added to in each case 10 g of the above polymer solutions in 1-acetoxy-2-ethoxyethane, which have been diluted with N,N-dimethylformamide, the amount of stabiliser (concentration) being based on the solids content. The polymer solutions containing the dissolved sensitiser are applied to copper-laminated epoxide plates by whirler-coating (500 revolutions/minute for 1 minute) so that after drying (15 minutes at 80° C.), a 1–3μ thick layer of polymer is formed on the copper. The coated plates are exposed through a negative original (step wedge: Stouffer 21 step sensitivity guide) as follows:

using a 400 watt high-pressure mercury lamp at a distance of 55 cm from the vacuum table, in front of which is a Pyrex glass filter 8 mm thick; for the exposure times, see Tables II–V.

with a 1000 watt metal halide lamp at a distance of 60 cm from the vacuum table; for the exposure times, see Table V.

After the exposure, the image is developed in a 1,1,1-trichloroethane bath over a period of 2 minutes, the non-crosslinked portions being dissolved out. The resulting relief image of the step wedge reproduced is rendered visible by etching the blank copper areas with 50% FeCl$_3$ solution. In Tables II–V which follow, S$_{rel}$ is the relative sensitivity. It is a factor which indicates by how much longer or shorter than 3 minutes exposure must be carried out in order to reproduce step 7 (optical density of the step wedge=1). The following relationship applies:

$$S_{rel} = \frac{1}{\sqrt{2}^{7-X}},$$

in which X is the step actually reproduced after 3 minutes exposure. The determination of S$_{rel}$ is based on the method described by W. S. De Forest ("Photoresist", McGraw-Hill Book Company, New York, 1975, pages 113 et seq.) for determining photosensitivity.

TABLE II

| Polymer 1, exposed with a 400 watt high-pressure mercury lamp | | | | | | | | | |
|---|---|---|---|---|---|---|---|---|---|
| | | | Sensitiser concentration | | Photosensitivity last step reproduced after | | | | |
| Sensitiser | | λmax. | εmax. | % by weight | mol % | 30″ | 1′ | 3′ | 6′ | S$_{rel}$ |
| [structure with COOC$_2$H$_5$ and NO$_2$] | | 411 | 4350 | 1.38 | 0.0042 | 5 | 7 | 10 | 12 | 2.83 |
| [structure with COOC$_2$H$_5$ and SO$_2$-phenyl] | | 401 | 5760 | 1.38 | 0.0032 | 3 | 6 | 9 | 10 | 2.00 |
| [structure with COOC$_2$H$_5$ and Cl] | | 382 | 6440 | 1.38 | 0.0043 | 2 | 4 | 8 | 10 | 1.41 |

TABLE II-continued

| Polymer 1, exposed with a 400 watt high-pressure mercury lamp | | | | | | | | | | |
|---|---|---|---|---|---|---|---|---|---|---|
| | | | Sensitiser concentration | | Photosensitivity last step reproduced after | | | | | |
| Sensitiser | | λmax. | εmax. | % by weight | mol % | 30" | 1' | 3' | 6' | $S_{rel}$ |
| 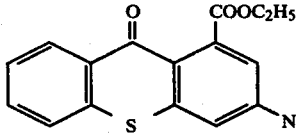 | | 381 | 6060 | 1.38 | 0.0038 | — | — | 3 | 5 | 0.25 |
| 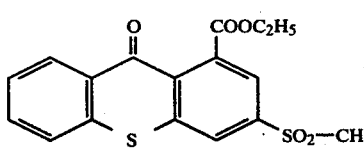 | | 399 | 5970 | 1.38 | 0.0038 | 4 | 6 | 10 | 11 | 2.83 |
| 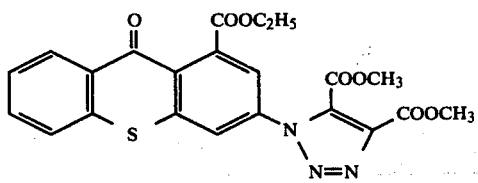 | | 391 | 6160 | 1.38 | 0.0030 | 2 | 5 | 8 | 10 | 1.41 |

TABLE III

| Polymer 2, exposed with a 400 watt high-pressure mercury lamp | | | | | | | | | |
|---|---|---|---|---|---|---|---|---|---|
| | | | Sensitiser concentration | | Photosensitivity last step reproduced after | | | | |
| Sensitiser | | λmax. | εmax. | % by weight | mol % | 1' | 3' | 6' | $S_{absolute}$ |
| 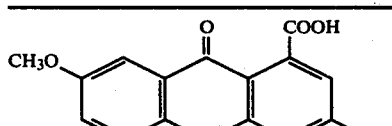 | | 434 | 3700 | 1.66 | 0.005 | 1 | 5 | 6 | 143% |
| 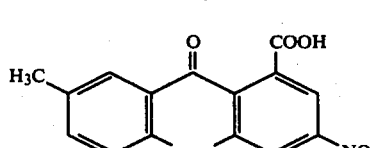 | | 420 | 4000 | 1.58 | 0.005 | 3 | 6 | 8 | 203% |
| 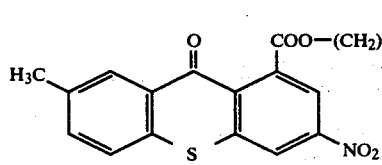 | | 420 | 4150 | 1.86 | 0.005 | 4 | 8 | 10 | 403% |
| 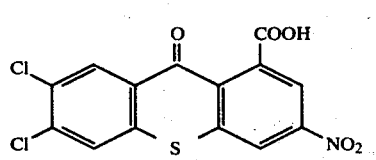 | | 410 | 4000 | 1.85 | 0.005 | 4 | 7 | 9 | 286% |
| 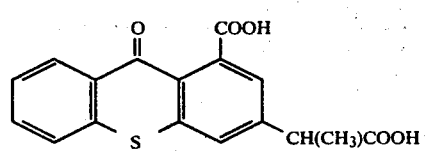 | | 384 | 5480 | 1.64 | 0.005 | 1 | 5 | 7 | 143% |

TABLE III-continued

Polymer 2, exposed with a 400 watt high-pressure mercury lamp

| Sensitiser | λmax. | εmax. | Sensitiser concentration % by weight | mol % | Photosensitivity last step reproduced after 1' | 3' | 6' | $S_{absolute}$ |
|---|---|---|---|---|---|---|---|---|
| 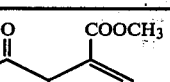 (structure with COOH, CH₂COOH, S) | 384 | 1840 | 1.57 | 0.005 | 1 | 5 | 7 | 143% |
| (structure with COO(CH₂)₃CH₃, Br, S) | 383 | 6000 | 1.96 | 0.005 | 2 | 6 | 8 | 203% |
| (structure with COOH, Cl, S) | 382 | 5800 | 1.45 | 0.005 | 2 | 5 | 5 | 143% |

TABLE IV

Polymer 3, exposed with a 400 watt high-pressure mercury lamp

| Sensitiser | λmax. | εmax. | Sensitiser concentration % by weight | mol % | Photosensitivity last step reproduced after 30" | 1' | 3' | 6' | $S_{rel}$ |
|---|---|---|---|---|---|---|---|---|---|
| 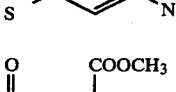 (structure with COOCH₃, NO₂, S) | 411 | 4380 | 1.38 | 0.0044 | 5 | 7 | 10 | 13 | 2.83 |
| (structure with COOCH₃, OCH₃, S) | 308 | 3000 | 1.38 | 0.0046 | 1 | 4 | 7 | 9 | 1.00 |

TABLE V

Polymer 4, exposed with a 400 watt high-pressure mercury lamp or a 1000 watt metal halide lamp

| Sensitiser | λmax. | εmax. | Sensitiser concentration % by weight | mol % | 400 W high-pressure mercury lamp last step reproduced after 6' | 12' | $S_{rel}$ | 1000 W metal halide lamp last step reproduced after 30" | 2' | 3' | $S_{rel}$ |
|---|---|---|---|---|---|---|---|---|---|---|---|
|  (structure with CONH—C₄H₉, NO₂, S, H₃C) | 421 | 4240 | 1.38 | 0.0373 | 5 | 7 | 0.25 | — | 5 | 5 | 0.5 |

TABLE V-continued
Polymer 4, exposed with a 400 watt high-pressure mercury lamp or a 1000 watt metal halide lamp
| Sensitiser | λmax. | εmax. | Sensitiser concentration % by weight | mol % | 400 W high-pressure mercury lamp last step reproduced after 6' | 12' | $S_{rel}$ | 1000 W metal halide lamp last step reproduced after 30" | 2' | 3' | $S_{rel}$ |
|---|---|---|---|---|---|---|---|---|---|---|---|
| 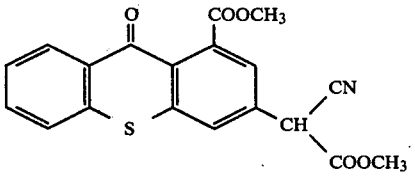 | 394 | 5900 | 1.38 | 0.0376 | 5 | 7 | 0.25 | 3 | 7 | 7 | 1 |
| 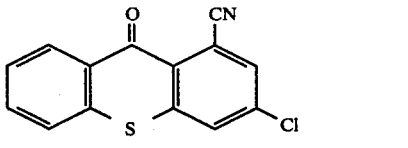 | 384 / 397 | 5240 / 5560 | 1.38 | 0.0051 | 6 | 7 | 0.35 | 3 | 7 | 8 | 1.41 |
| 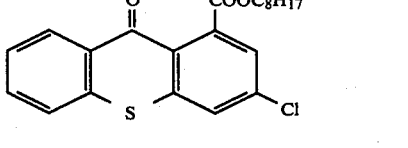 | 382 | 6320 | 1.38 | 0.0034 | 4 | 6 | 0.18 | 1 | 5 | 6 | 0.71 |
| 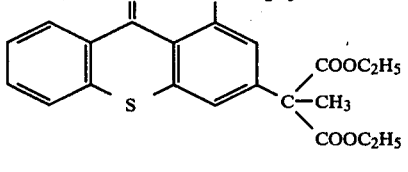 | 384 | 6600 | 1.38 | 0.0030 | 5 | 6 | 0.25 | 1 | 6 | 7 | 1 |
| 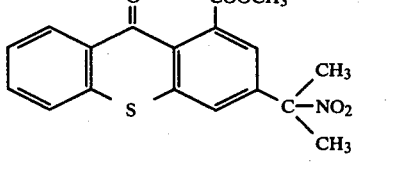 | 387 | 6320 | 1.38 | 0.0039 | 5 | 7 | 0.25 | 1 | 5 | 7 | 1 |
| 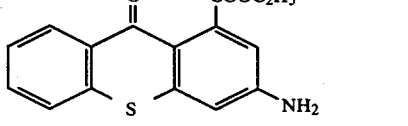 | 353 | 12780 | 1.38 | 0.0046 | 4 | 6 | 0.18 | — | 4 | 5 | 0.5 |
| 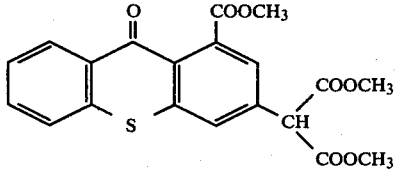 | 386 | 6520 | 1.38 | 0.0034 | 5 | 6 | 0.25 | 2 | 6 | 7 | 1 |
| 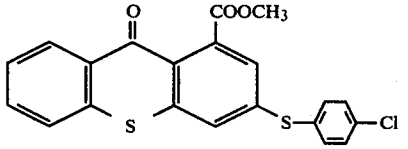 | 368 / 380 | 6820 / 6680 | 1.38 | 0.0033 | 5 | 7 | 0.25 | 2 | 5 | 7 | 1 |

TABLE V-continued

Polymer 4, exposed with a 400 watt high-pressure mercury lamp or a 1000 watt metal halide lamp

| Sensitiser | λmax. | εmax. | Sensitiser concentration | | 400 W high-pressure mercury lamp | | | 1000 W metal halide lamp | | | |
|---|---|---|---|---|---|---|---|---|---|---|---|
| | | | % by weight | mol % | last step reproduced after | | $S_{rel}$ | last step reproduced after | | | $S_{rel}$ |
| | | | | | 6' | 12' | | 30" | 2' | 3' | |
|  | 370 | 6080 | 1.38 | 0.0042 | 4 | 6 | 0.18 | 1 | 5 | 6 | 0.71 |

Example II

A white lacquer is prepared in accordance with the following recipe:
30.0 g of "PLEX 6631" (acrylic resin from Röhm and Haas, Federal Republic of Germany)
14.0 g of trismethylolpropane triacrylate
14.0 g of neopentylglycolpropane triacrylate
1.16 g of N-methyldiethanolamine.

In each case 0.4 g of the photo-initiators listed below is added to 9.6 g of this mixture. The lacquer prepared in this way is applied to glass plates using a 40 μm doctor. The samples are irradiated using a UV exposure apparatus (standard Hg vapour lamp, lamp power: 80 W/cm, distance of the lamp from the plate: 11 cm, conveyor belt speed: 50 m/minute). The wiping resistance is used as a test to assess the irradiated lacquer samples. The number of passes of the samples through the irradiation apparatus before a wipe-resistant surface is obtained is determined.

| Photo-initiator | Wiping resistance |
|---|---|
| 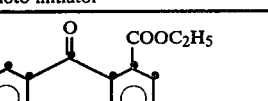 | 3 × |
| 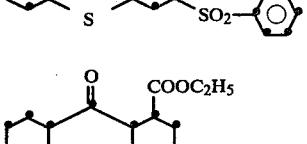 | 2 × |

What is claimed is:
1. A compound of the formula I

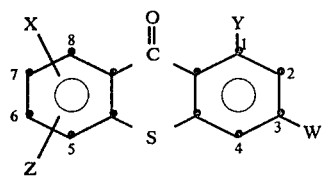

(I)

in which W is halogen, —CN, —OH, —N(R$_1$)(R$_2$), —NO$_2$, phenylsulfonyl, toluylsulfonyl, C$_{1-4}$-alkylsulfonyl, C$_{1-10}$-alkoxy, C$_{1-10}$-alkylthio, C$_{1-12}$-halogenoalkylthio, phenoxy, toluyloxy, phenylthio, chlorophenylthio, toluylthio, azido, 4,5-bis-C$_{1-2}$-alkoxycarbonyl-1,2,3-triazolyl, C$_{3-5}$-alkenyloxy, C$_{3-5}$-alkynyloxy, 1-nitroalkyl having 1–5 C atoms, —CH(COOR$_3$)$_2$, —C(-COOR$_3$)$_2$(CH$_3$), —CH(CN)(COOR$_3$), —C(CN)-(COOR$_3$)(CH$_3$), —CH(CN)$_2$, —C(CN)$_2$(CH$_3$), —CH$_2$COOH or —CH(CH$_3$)(COOH), Y is —CO-halogen, —COOR$_1$, —COSR$_1$, —CON(R$_1$)(R$_2$), —CO-piperidyl, —CO-pyrrolidinyl, —CO-morpholinyl or —CN, Z is hydrogen, halogen, —OH or alkyl, alkoxy, alkylthio or N,N-dialkylamino having in each case 1–4 C atoms in the alkyl groups, X can have the same meaning as W or is hydrogen, —SO$_3$H, alkyl, —NHCO-alkyl or —CO-alkyl having in each case 1–4 C atoms in the alkyl group, —COOR$_1$, —COSR$_1$, —CON(R$_1$)(R$_2$), —CO-piperidyl, —CO-pyrrolidinyl or —CO-morpholinyl, R$_1$ is hydrogen, C$_{1-20}$-alkyl, C$_{5-12}$-cycloalkyl, phenyl, naphthyl or benzyl, R$_2$ is hydrogen or C$_{1-20}$-alkyl and R$_3$ is methyl or ethyl.

2. A compound of the formula I according to claim 1, in which Y is other than —CO-halogen.

3. A compound of the formula I according to claim 1, in which W is halogen, —CN, —N(R$_1$)(R$_2$), in which R$_1$ and R$_2$ independently of one another are hydrogen or C$_{1-4}$-alkyl, or NO$_2$, phenylsulfonyl, p-toluylsulfonyl, C$_{1-4}$-alkylsulfonyl, C$_{1-4}$-alkoxy, C$_{1-4}$-alkylthio, —SCH$_2$CH$_2$-(CF$_2$)$_n$F, in which n is 4, 6, 8 or 10, phenoxy, p-toluyloxy, phenylthio, p-chlorophenylthio, p-toluylthio, azido, 4,5-bis-(C$_{1-2}$-alkoxycarbonyl)-1,2,3-triazolyl, 1-nitroalkyl having 1–5 C atoms, —CH(COOR$_3$)$_2$, —C(COOR$_3$)$_2$(CH$_3$), —CH(CN)(COOR$_3$), —C(CN)(COOR$_3$)(CH$_3$), —CH(CN)$_2$, —C(CN)$_2$(CH$_3$), —CH$_2$COOH or —CH(CH$_3$)-(COOH), Y is —COOH, —CN, —COOalkyl having 1–8 C atoms in the alkyl moiety, —COSalkyl having 1–4 C atoms in the alkyl moiety or —CON(R$_1$)(R$_2$), in which R$_1$ and R$_2$ independently of one another are hydrogen or C$_{1-4}$-alkyl, Z is hydrogen, halogen or C$_{1-4}$-alkyl, X is hydrogen, C$_{1-4}$-alkyl, C$_{1-4}$-alkoxy, —COOalkyl having 1–8 C atoms in the alkyl moiety, —COSalkyl having 1–4 C atoms in the alkyl moiety or —CON(R$_1$)(R$_2$), in which R$_1$ and R$_2$ independently of one another are hydrogen or C$_{1-4}$-alkyl, and R$_3$ is methyl or ethyl.

4. A compound of the formula I according to claim 1, in which X is hydrogen, halogen, alkyl, alkoxy or alkylthio having in each case 1–4 C atoms, or acetylamino, Z is hydrogen, halogen or alkyl having 1–4 C atoms, W is chlorine, bromine, —NH$_2$, —NO$_2$, C$_{1-4}$-alkylsulfonyl, phenylsulfonyl, p-toluylsulfonyl, C$_{1-4}$-alkoxy, C$_{1-4}$- alkylthio, p-chlorophenylthio or 2-nitro-2-propyl and Y is —COOH, —CN, —COOalkyl having 1-8 C atoms in the alkyl moiety or —CON($R_1$)($R_2$), in which $R_1$ and $R_2$ independently of one another are $C_{1-4}$-alkyl or hydrogen.

5. A compound of the formula I according to claim 1, in which X is hydrogen, or methyl which is bonded in the 7-position, Z is hydrogen, W is chlorine, —$NO_2$ or phenylsulfonyl and Y is —COOH or —COOalkyl having 1-8 C atoms.

6. A compound of the formula I according to claim 1, in which X and Z are each hydrogen, W is the nitro group and Y is —COOH, —COO$CH_3$ or —COO$C_2H_5$.

* * * * *